(12) United States Patent
Hibasami et al.

(10) Patent No.: US 8,709,504 B2
(45) Date of Patent: Apr. 29, 2014

(54) APOPTOSIS INDUCTOR EXTRACTED FROM POTATO, POTATO FOODSTUFF CONTAINING THE INDUCTOR, AND PROCESSED PRODUCT THEREOF

(75) Inventors: Hiroshige Hibasami, Age (JP); Motoyuki Mori, Kasai (JP); Yoshio Oka, Tokyo (JP); Kazuya Hayashi, Tokyo (JP)

(73) Assignees: Hiroshige Hibasami, Age (JP); Wada Sugar Refining Co., Ltd., Tokyo (JP); Independent Administrative Institute, National Agricultural Research Organization (NARO), Tsukuba (JP)

( * ) Notice: Subject to any disclaimer, the term of this patent is extended or adjusted under 35 U.S.C. 154(b) by 339 days.

(21) Appl. No.: 12/976,625

(22) Filed: Dec. 22, 2010

(65) Prior Publication Data

US 2011/0092586 A1   Apr. 21, 2011

Related U.S. Application Data

(62) Division of application No. 10/456,480, filed on Jun. 9, 2003, now abandoned.

(30) Foreign Application Priority Data

Jul. 9, 2002   (JP) ................. 2002-199771

(51) Int. Cl.
  *A61K 36/00* (2006.01)
  *A61K 36/81* (2006.01)
(52) U.S. Cl.
  USPC ........................................... 424/725
(58) Field of Classification Search
  None
  See application file for complete search history.

(56) References Cited

U.S. PATENT DOCUMENTS 6,180,154 B1 * 1/2001 Wrolstad et al. ............. 426/540

FOREIGN PATENT DOCUMENTS

| JP | 59059624 | | | 4/1982 |
|---|---|---|---|---|
| JP | 60069025 | | | 4/1985 |
| JP | 60069025 | A | * | 4/1985 |
| JP | 10204312 | A | * | 8/1998 |
| JP | 11332525 | | | 12/1999 |
| JP | 2001-321103 | | | 11/2001 |
| JP | 2001316399 | | | 11/2001 |
| JP | 2001-346541 | | | 12/2001 |
| JP | 0200134654 | | | 12/2001 |
| JP | 2001346541 | A | * | 12/2001 |
| JP | 2002-230 | | | 1/2002 |
| JP | 2003-277271 | | | 10/2003 |
| WO | WO 97/41137 | | | 11/1997 |
| WO | WO 9741137 | A1 | * | 11/1997 |

OTHER PUBLICATIONS

T. Ko, et al., "Anticancer Promotion Activity of the Extracts From Blue Berry and Purple Sweet Potato and Their Induction of Apoptosis of Cancer Cells", 3, 5, 2002, p. 245 (4-3Ba07), (with English Translation).

Akihiro Hagiwara, et al., "Prevention by Natural Food Anthocyanins, Purple Sweet Potato Color and Red Cabbage Color, of 2-Amino-1-Methyl-6-Phenylimidazo[4,5-b]Pyridine (PhIP)-Associated Colorectal Carcinogenesis in Rats Initiated With 1,2-Dimethylhydrazine", The Journal of Toxicological Sciences, vol. 27, No. 1, Feb. 2002, pp. 57-68.

Hayashi et al., Kinjiso (Gynura bicolor DC) colored extract induce apoptosis in HL60 leukemia cells. Nippon Shokuhin Kagaku Kogaku Kaishi, 49 (8): 519-526, 2002.

* cited by examiner

*Primary Examiner* — Qiuwen Mi
(74) *Attorney, Agent, or Firm* — Oblon, Spivak, McClelland, Maier & Neustadt, L.L.P.

(57) ABSTRACT

An apoptosis inductor is formed of an anthocyanin-containing extract obtained from a potato containing anthocyanine in the skin and flesh thereof. The potato is a potato of cultivated species, such as *Solanum tuberosum* ssp. *andigena* L. and *S. phureja* Juz. et Buk., or of hybrid species based on the cultivated species.

19 Claims, 8 Drawing Sheets

FIG.3 (a)  FIG.3 (b)
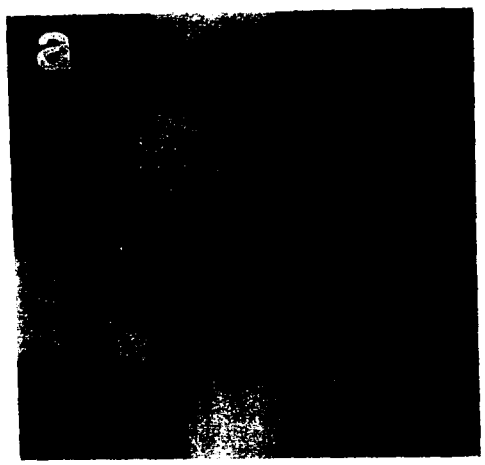
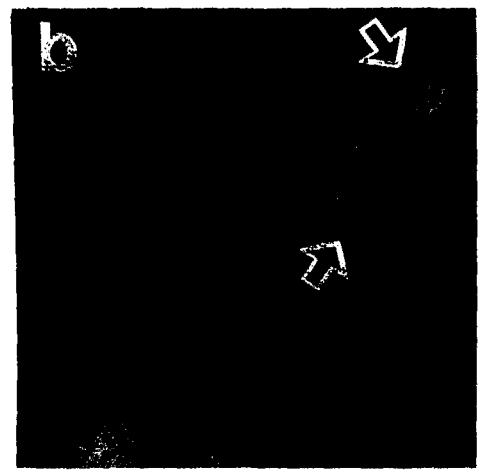
CONTROL
DRIED CRUDE
ANTHOCYANIN
EXTRACT (2.5mg/ml)

M     DNA MARKER
(1) CONTROL (50%,ETHANOL)
(2) CRUDE ANTHOCYANIN EXTRACT FROM INCA PURPLE (2.5mg/ml)
(3) PURIFIED ANTHOCYANIN POWER FROM INCA PURPLE (2.5mg/ml)
(4) CRUDE ANTHOCYANIN EXTRACT FROM INCA RED (2.5mg/ml)
(5) PURIFIED ANTHOCYANIN POWDER FROM INCA RED (2.5mg/ml)

| | |
|---|---|
| M | DNA MARKER |
| (1) | Control(50%.ETHANOL) |
| (2) | IP-A(1.25mg/ml) |
| (3) | IP-B(1.25mg/ml) |
| (4) | IP-C(1.25mg/ml) |
| (5) | IP-D(1.25mg/ml) |
| (6) | IR-A(1.25mg/ml) |
| (7) | IR-B(1.25mg/ml) |
| (8) | IR-C(1.25mg/ml) |
| (9) | IR-D(1.25mg/ml) |

# APOPTOSIS INDUCTOR EXTRACTED FROM POTATO, POTATO FOODSTUFF CONTAINING THE INDUCTOR, AND PROCESSED PRODUCT THEREOF

This application is a Divisional of U.S. application Ser. No. 10/456,480, filed Jun. 9, 2003, abandoned.

BACKGROUND OF THE INVENTION

1. Field of the Invention

This invention relates to an apoptosis inductor extracted as a particularly effective substance against cancer from anthocyanin-containing potato, a potato foodstuff containing the inductor, and a processed product thereof.

2. Description of the Prior Art

At present, cancers are diseases that are leading all the causes for death. The prevention of cancer, therefore, has been arousing a truly profound concern in most people. Thus, many daily practicable methods for effecting prevention of cancer have been being proposed.

In recent years, the researches concerning apoptosis, namely the suicide of cancer cells, have been gaining in enthusiasm in the field of cancer study. The fact that the apoptosis not only discharges an important role in the formation of tissues and internal organs during the generation of living individuals and in the maintenance and defense of the homeostasis of living organisms but also relates deeply to the incidence of numerous diseases has been being elucidated. The abnormality of the action of the apoptosis in the control of cells is thought to form one of the causes for the development of cancer. It is held that when the cells that are inherently doomed to perish happen to survive the apoptosis, namely their own suicide, they encounter various stimulations and consequently undergo repetitive displacements on chromosomes and ultimately turn into cancer cells. The cancer cells are enabled to proliferate only after they acquire the mechanism of resistance of the apoptosis. From this fact, it is logical to conclude that the process in which cells cancerate in consequence of a varying displacement of genes is related to the process in which the resistance to apoptosis is acquired.

As the means to prevent cancer, numerous eatables and drinkables have been proposed. It is known that among other eatables and drinkables, the existing carcinostatic agents are particularly possessed of the activity of inducing apoptosis on cancer cells.

The existing carcinostatic agents, however, are synthetic chemical substances. They are at a disadvantage in being inevitably expensive because they require time and cost copiously for research and development, in not allowing easy determination of proper dosage, and in rendering protracted use difficult. Further, since most existing carcinostatic agents are synthetic products, they manifest strong adverse reactions and these side effects impose a great burden on patients suffering from cancers.

This invention is directed toward providing a substance which enjoys inexpensiveness as compared with the conventional carcinostatic agents, manifests practically no side effect, and possesses such an action of controlling cancer as permits continuous ingestion.

SUMMARY OF THE INVENTION

This invention provides an apoptosis inductor formed of an anthocyanin-containing extract obtained from a potato containing anthocyanin in skin and flesh.

In the apoptosis inductor, the potato is a potato of cultivated species, such as *Solanum tuberosum* ssp. *andigena* L. and *S. phureja* Juz. et Buk., or of hybrid species based on the cultivated species.

This invention also provides a potato foodstuff containing the apoptosis inductor and exhibiting a color capable of being expressed with the apoptosis.

The invention further provides a processed product of potato containing the apoptosis inductor.

Since the apoptosis inductor of this invention uses as the raw material for it such potatoes as contain the anthocyanin which is a component originating in natural food and which the mankind have long been accustomed to take as food since long ago, it neither suffers from expensiveness nor manifests an unwanted side effect unlike the conventional carcinostatic agents but enjoys truly high safety enough to permit continuous ingestion. Further, since it exhibits an excellent tinting property, it can be manufactured into a colored food and therefore can be used for enhancing a visual effect particularly where it is elected to be consumed as included in a varying kind of food.

BRIEF EXPLANATION OF THE DRAWING

FIG. 3(a) is a copy of an optical electron microphotograph showing a control, and FIG. 3(b) is that showing a morphometric change caused in the cells of the stomach cancer by the dried crude anthocyanin extract.

DESCRIPTION OF THE PREFERRED EMBODIMENT

Figure 1:
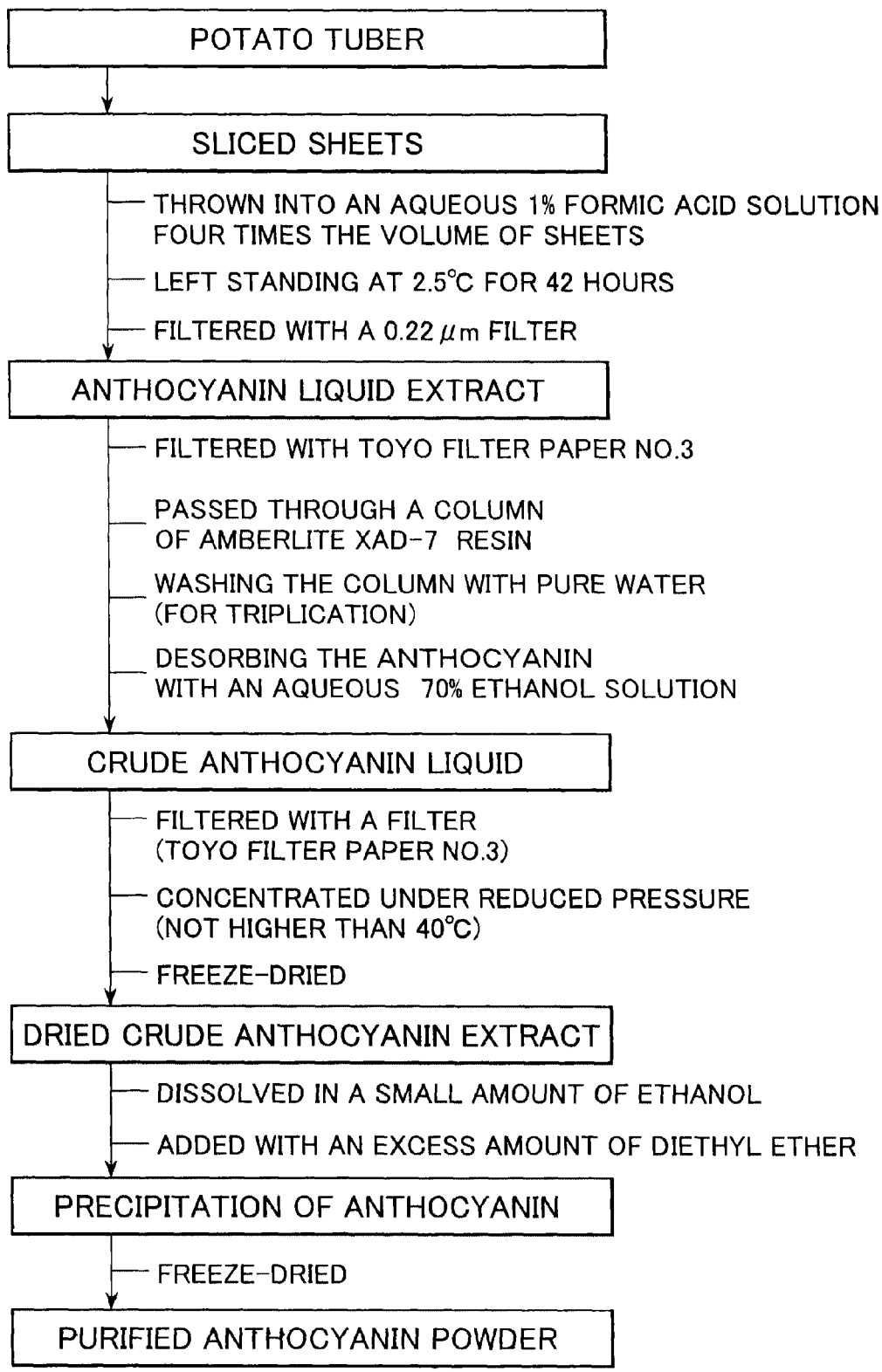
FIG. 1 is a schematic process diagram illustrating one method for producing an apoptosis inductor contained in the anthocyanin originating in potatoes as one example of this invention.

The apoptosis inductor according to this invention is an anthocyanin-containing extract originating in potatoes that contain anthocyanin in the skin and the flesh. The method employed for the production of this inductor, therefore, is required to resort mainly to the extraction of the anthocyanin as described in detail below.

As concrete examples of the anthocyanin-containing potato, there can be cited potatoes of cultivated species, such as *Solanum tuberosum* ssp. *andigena* L. and *S. phureja* Juz. et Buk., and potatoes of hybrid species based on the cultivated species, such as Inca red and Inca purple.

The extraction of the anthocyanin from raw materials, such as ordinary purple sweet potatoes and red cabbages, is implemented by the use of an aqueous 0.5% sulfuric acid solution at room temperature. Specifically under these conditions, the anthocyanine is effectively extracted without entailing a very serious problem when purple sweet potatoes and red cabbages are used as raw materials.

The potatoes mentioned above, however, have an oxidizing enzyme, such as polyphenol oxidase (tyrosinase), which browns polyphenol occurring in their tubers. The enzymatic activity of this oxidizing enzyme is so strong as to discolor and decompose the anthocyanin easily. Further, the anthocyanin originating in potatoes exhibits no perfect stability even in a dilute state as compared with the anthocyanin originating in purple sweet potatoes and red cabbages.

When the apoptosis inductor contemplated by this invention, namely the anthocyanin-containing extract originating in potatoes, is required to be obtained from the tubers of such potatoes, therefore, such a method as has been heretofore applied to purple sweet potatoes and red cabbages encounters difficulty in ensuring stable and efficient acquisition of the anthocyanin without inducing a structural change in the anthocyanin.

In the extraction of the anthocyanin from the tubers of the potatoes of hybrid species, such as Inca red and Inca purple, which contain the anthocyanin, an acid or an acid alcohol is used as an extracting solvent. As concrete examples of the condition for stopping the activity of the oxidizing enzyme, acidifying the reaction system to not more than pH 3.0, effecting the extraction at a temperature of not higher than 10° C. (preferably not higher than 4° C.), and using an alcohol of a concentration of not less than 50% for the extraction may be cited. While lactic acid, acetic acid and citric acid are usable as the extracting solvent, it is preferable to use formic acid or trifluoroacetic acid for the purpose of more enhancing the efficiency of extraction and the stability of anthocyanin. The concentration of such an acid is in the approximate range of 1 to 5%. It is commendable to add to the extracting liquid not less than 1%, preferably about 5%, of table salt.

Now, one preferred example of the extraction of the apoptosis inductor of this invention (the anthocyanin-containing extract originating in chromatic potatoes) from potatoes containing the anthocyanin will be explained.

First, the tubers of potatoes containing anthocyanin are sliced as with a slicer into sheets about 2 mm in thickness and the freshly sliced sheets of tubers are directly thrown into an anthocyanin-extracting liquid about four times as large as the total volume of the sheets eventually placed in the liquid with the object of preventing the sliced sheets of tubers from discoloration. In this case, an aqueous 3% formic acid solution containing 1% of table salt is used as the anthocyanin-extracting liquid. The anthocyanin-extracting temperature and the temperature of the anthocyanin-extracting liquid are both set during the course of the extraction at 10° C., i.e. the level at which the oxidizing enzyme fails to function.

Next, the anthocyanin liquid extract obtained as described above is subjected to a solid-liquid separating treatment, such as filtration or centrifugation, to expel solid particles and obtain a crude anthocyanin liquid. Further, the flavonoid type components including the anthocyanin in the crude anthocyanin liquid are adsorbed on a synthetic adsorbent resin, such as a methacrylic ester type resin made by Japan Organo K.K. and sold under the trademark designation of "Amberlite XAD-7" or a styrene-divinylbenzene type resin made by Mitsubishi Kasai K.K. and sold under the product code of "HP-20", and the component adsorbed on the resin is desorbed with ethanol. For the elution of the components, organic solvents, such as alcohols represented by methanol and isopropanol, and acetonitrile and further mixtures of such organic solvents with water (preferably containing such an organic solvent in a concentration of not less than 50% by weight) may be used.

Subsequently, the crude anthocyanin liquid treated with the adsorbent resin is either freeze-dried or dried under reduced pressure at a temperature of not higher than 40° C. to obtain a dried crude anthocyanin extract in the form of a powder. Further, the dried crude anthocyanin extract powder is dissolved in a small amount of 99.9% ethanol and the resultant solution and an excess amount of diethyl ether are added together to induce forced precipitation of the anthocyanin. The precipitate thus produced is either dried under reduced pressure at a temperature of not higher than 40° C. or freeze-dried to obtain a purified anthocyanin powder.

One example of the specific process starting with the step of slicing potatoes and ending with the step of obtaining the purified anthocyanin powder is illustrated in FIG. 1.

The term "apoptosis inductor" used in this invention embraces the crude anthocyanin liquid, the dried crude anthocyanin extract resulting from drying, and also the purified anthocyanin powder resulting from purifying the dried crude anthocyanin extract, as indicated in FIG. 1.

The anthocyanin-containing extract mentioned above may be processed into drinkables. These drinkables may be directly ingested daily as though they were sport drinks or tea beverages or they may be further added to various foodstuffs and ingested as health foods or specific health promoting foods. Otherwise, the anthocyanin-containing extract may be processed into capsules, tablets and syrups like vitamin preparations so as to permit deliberate ingestion of this substance. Specifically, the processed products of the apoptosis inductor of this invention are allowed to assume various forms, such as drinkables, eatables, capsules, tablets and syrups. Further, by utilizing the tinge that inheres in the apoptosis inductor (the anthocyanin-containing extract) itself, the processed products of this inductor may be tinted in colors which foods are preferred to assume so as to enhance the tastes of such processed products visually.

Now, examples of this invention will be described below. It should be noted that this invention is not restricted to the following examples.

Example 1

Anthocyanin-containing extracts from anthocyanin-containing potatoes of the species of Inca red and Inca purple were tested in Experiments 1 to 3, shown below, serving to investigate the effect of repressing propagation of the cells of the cancer of the human stomach with the object of confirming the function of inducing apoptosis.

The anthocyanin-containing extracts were obtained from the potatoes by following the method of extraction mentioned above with necessary modifications.

The tuber of potato was sliced with a slicer into sheets 2 mm in thickness. The sheets of tuber were placed in an aqueous 3% formic acid solution to induce extraction of anthocyanin therefrom. The solution containing the extract was passed through a column of an XAD-7 resin to cause adsorption of the anthocyanin on the resin. The anthocyanin adsorbed on the resin was desorbed with an alcohol.

The desorbed anthocyanin was passed through a filter, and the filtered anthocyanin was dried under reduced pressure to obtain dried crude anthocyanin extracts respectively from the Inca red and Inca purple. The dried crude anthocyanin extracts were dissolved in an alcohol, the resultant solution was passed through a filter to expel solid particles, the remaining solution was dried under reduced pressure, and thereafter the dried mass was reduced to purified anthocyanin powders of Inca red and Inca purple.

Experiment 1

Figure 2:
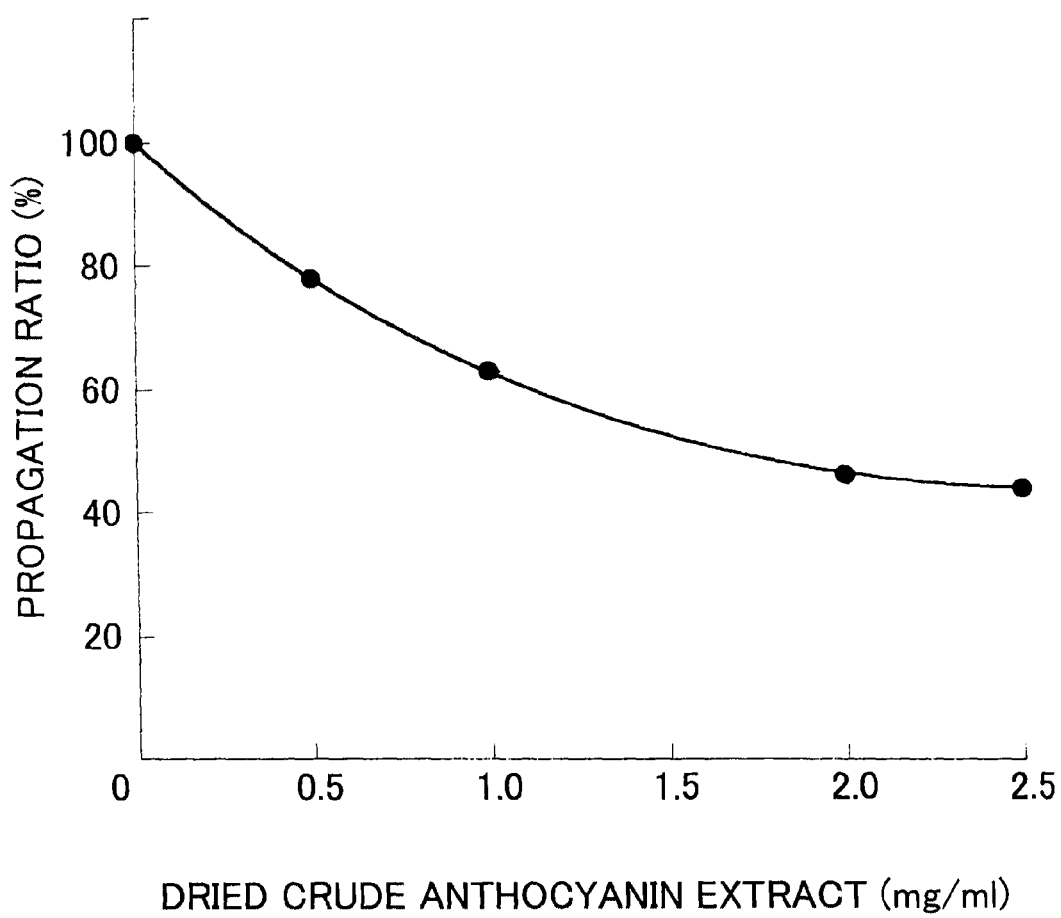
FIG. 2 is a graph showing the action exhibited by the dried crude anthocyanin extract in controlling the proliferation of the cells of the human cancer.

Cells of human stomach cancer were cultured in an RPMI1640 medium containing 10% bovine fetal blood serum as adjusted to a density of $5 \times 10^5$/ml. One group of culture broths having an aqueous 50% ethanol solution added thereto (control group) and another group of culture broths having a solution of the dried crude anthocyanin extract from Inca red in an aqueous 50% ethanol solution added thereto (experiment group) were respectively cultured for three days under the conditions of 37° C. and 95% to 5% $CO_2$. During the course of this culture, the cells of stomach cancer were counted every day to obtain a curve of the propagation of stomach cancer cells. The results were as shown in FIG. 2. The culture broths under culture were so adjusted as to have final dried crude anthocyanin extract concentrations of 0.5 mg/ml, 1.0 mg/ml, 1.5 mg/ml, 2.0 mg/ml and 2.5 mg/ml.

It is clear from FIG. 2 that the function of the dried crude anthocyanin extract to induce apoptosis was confirmed by the fact that the effect manifested by this extract in repressing the propagation of human stomach cancer cells grew in proportion to the increase in the concentration thereof.

Experiment 2

The stomach cancer cells of the control group and the experiment group cultured in Experiment 1 were tinted with a coloring matter and photographed. The photographs thus obtained are shown in FIG. 3(a) and FIG. 3(b), respectively.

It is clear from the comparison of FIG. 3(a) with FIG. 3(b) that the function of the dried crude anthocyanin extract to induce apoptosis was confirmed by the fact that the stomach cancer cells were brought to nearly complete extinction in the experiment using the extract at a daily dosage of 2.5 mg/ml for three days.

Experiment 3

Figure 4:
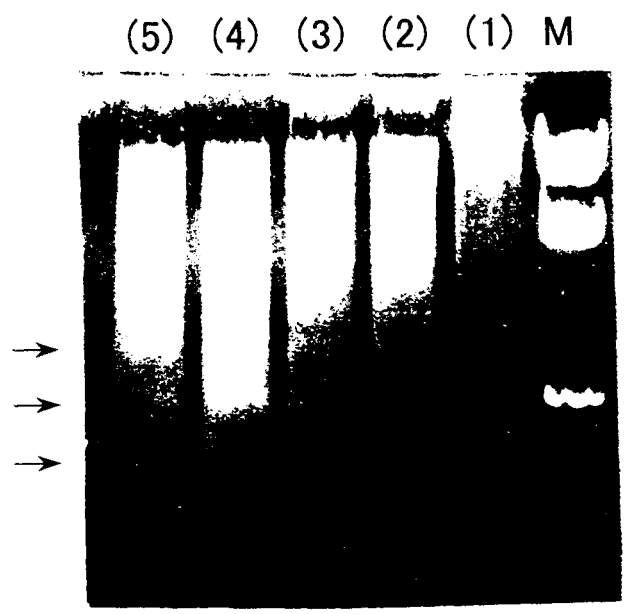
FIG. 4 is a copy of a photograph showing the state of distribution of the DNA segmented by crude anthocyanin extracts and purified anthocyanin powders.

The stomach cancer cells of the control group and the experiment group cultured in Experiment 1 were each centrifuged to expel the supernatant and obtain residual cells. The residual cells were washed once with PBS (−). The washed cells contained in the cell pellets were dissolved with a cell-melting buffer added to the pellets and, by the addition of an RNAse solution thereto, made to react with the RNAse at 50° C. for 2.5 hours and, by the addition of a protease K solution thereto, made to react with the protease K at 50° C. for 2.5 hours. From the cell pellets that had undergone these reactions, DNA segments were extracted. The DNA extracts were each mixed with a gel-loading liquid, and the resultant mixtures were placed one each in the wells of a 2% agarose gel plate and subjected to electrophoresis at 100 V. After the gel plate was immersed in water, the wet mixtures in the wells were scanned with a UV transilluminator to detect DNAs emitting ethidium bromide fluorescence. The photographs showing the results of this scanning are shown in FIG. 4. The symbol "M" placed in FIG. 4 denotes a DNA molecular weight marker.

It is clear from FIG. 4 that the dried crude anthocyanin extract (2) obtained from Inca purple, the purified anthocyanin powder (3) derived from the extract (2), the dried crude anthocyanin extract (4) derived from Inca red, and the purified anthocyanin powder (5) derived from the extract (4) invariably inhibited the propagation of human stomach cancer cells and that the apoptosis, i.e. a mechanism embodying the inhibition of propagation, brought the stomach cancer cells to extinction through segmentation of DNA. It is also noted that the function of repressing the propagation gained in intensity and the amount of DNA segments increased in proportion as the amount of the apoptosis inductor to be added increased.

Example 2

The ingestion of fresh tubers containing an anthocyanin-containing extract exhibiting the ability to induce apoptosis was tested to determine the function of depressing cancer in Experiment 4 below and the effect was consequently confirmed.

Experiment 4

The mice whose stomachs had been made to assume a precancerous state by the injection of a solution of benzo (α) pyrene in olive into the stomachs of the mice with a probe were left voluntarily feeding on steamed tubers of Inca purple and Inca red for five months. After this programmed ingestion, the mice were each examined to determine the number of tumors developed in the stomach and the weights of such tumors. Common potatoes (Irish Cobbler) were used for control.

TABLE 1

Coefficient of Repression of Development of
Stomach Cancer by Ingestion of Steamed Tubers

| Sample | Number of Tumors/Mouth | Tumor/Mouth (g) | Coefficient of Repression (%) |
|---|---|---|---|
| Irish Cobbler | 4.9 ± 1.1 | 0.13 ± 0.04 | — |
| Inca red | 3.3 ± 1.1 | 0.07 ± 0.03 | 46.2 |
| Inca purple | 4.1 ± 0.9 | 0.08 ± 0.02 | 38.5 |

Coefficient of repression of development of stomach cancer (%) = {1 − [Weight of tumors (g) of stomach cancer in mouse having ingested Inca red or Inca purple]/[Weight of tumors (g) of stomach cancer in mouse having ingested Irish Cobbler potato]} × 100

It is clear from Table 1 above that Inca red showed 46.2% and Inca purple 38.5% respectively of repression of the number of tumors of stomach cancer and the weight of such tumors as compared with Irish Cobbler. It is further clear that the development of stomach cancer was repressed also when the same potatoes in a cooked state were orally administered.

Example 3

Figure 5:
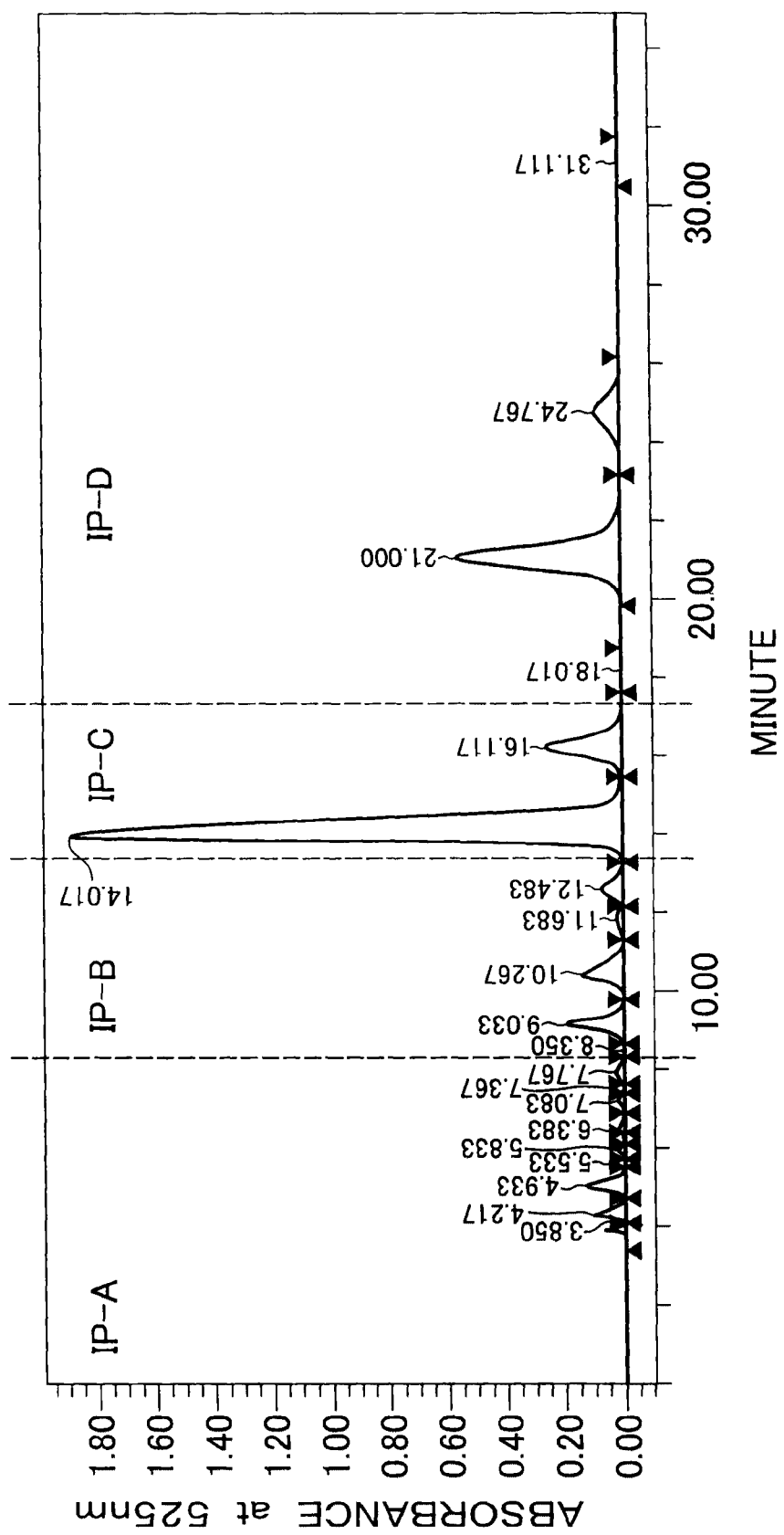
FIG. 5 is a graph showing fractions obtained by fractionating the dried crude anthocyanin extract from Inca purple through a high-speed liquid chromatography.
Figure 6:
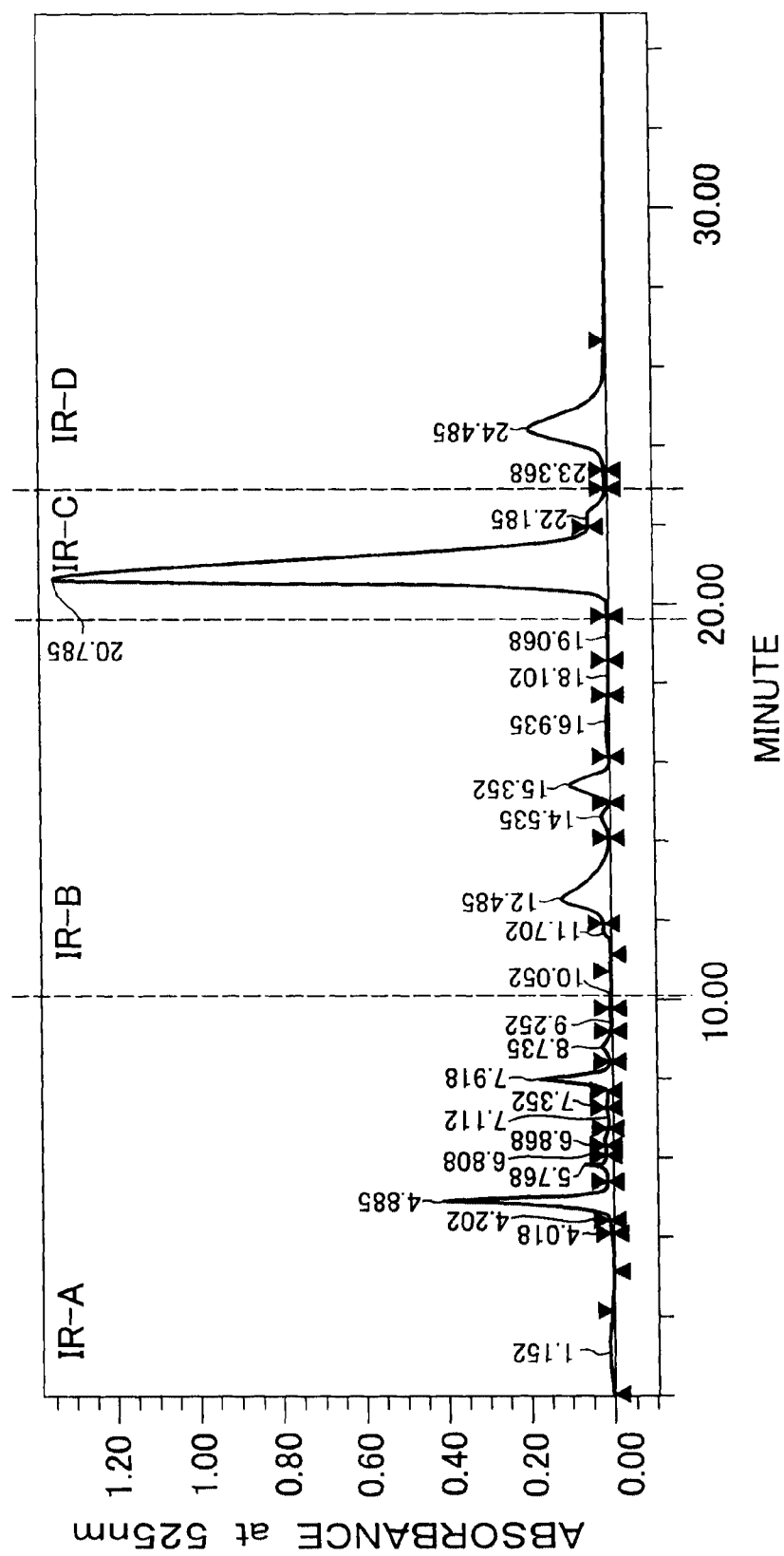
FIG. 6 is a graph showing fractions obtained by fractionating the dried crude anthocyanin extract from Inca red through a high-speed liquid chromatography.
Figure 7:
FIG. 7 is a copy of a photograph showing the state of distribution of the DNA of the fractions of FIG. 5 and FIG. 6 segmented by potato anthocyanin.

Dried crude anthocyanin extracts from Inca purple and Inca red were fractionated through a high-speed liquid chromatography to obtain fractions (FIG. 5 and FIG. 6), and stomach cancer cell DNA of each fraction segmented by apoptosis was tested for the state of distribution. As shown in FIG. 7, in fraction IP-B of the Inca purple extract and fraction IR-A of the Inca red extract, DNA segmentation was observed. It is thus found that fractions relatively rapid to elute exhibit the activity of inducing apoptosis, and these fractions are mixtures having no organic acid bond and containing some kinds of non-acylated anthocianin as the principal components.

Example 4

Figure 8:
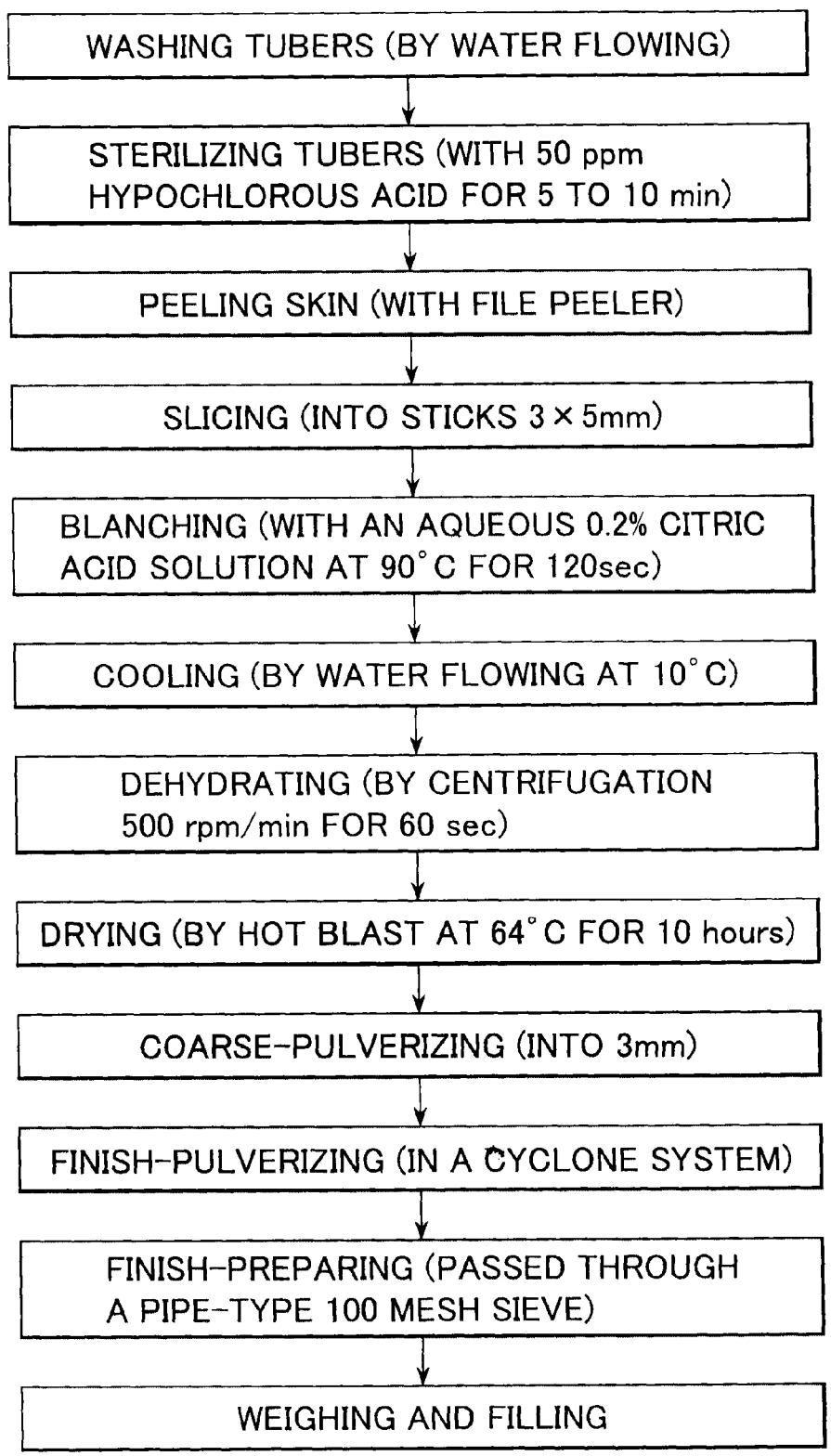
FIG. 8 is a flow chart showing the process of producing dried anthocyanin extracts and purified powders in Example 4.

The ingestion of Inca-purple and Inca-red purified anthocyanin powders obtained from crude Inca purple extract, crude Inca red extract, Inca purple and Inca red through the method disclosed in FIG. 8 and exhibiting the ability to induce apoptosis was tested to determine the function of depressing cancer in Experiment 5 below, and the effect was consequently confirmed.

Experiment 5

A solution of 1.5 mg of benzo (α) pyrene in 100 μl of corn oil was injected into the stomachs of the inbred strain mice (male) with a probe once a week for four weeks. Subsequently, while the control group was fed with tap water only, the experiment group was continuously dosed for five months with a sample suspended and dissolved to have the concentration shown in Table 2 below using a feeding bottle. Upon confirming the presence of stomach cancer tumors, the stomach was removed, expanded and fixed on aluminum foil and examined to count the number of tumors (not less than 2 mm in diameter) and determine the number of tumors per mouth. In addition, the tumors were cut off and collected to measure the weights of such tumors and count the weight of the tumors per mouth.

TABLE 2

Coefficient of Repression of Development of Stomach Cancer by Ingestion of Purified Powder and Crude Anthocyanin

|  | Number of Tumors/Mouth | Weight of Tumor/Mouth (mg) |
| --- | --- | --- |
| Control Group (Water) | 9.6 ± 1.0 | 205 ± 15 |
| Inca Red Purified Powder (1%) | 5.4 ± 0.5 | 115 ± 13 |
| Inca Purple Purified Powder (1%) | 5.7 ± 0.4 | 118 ± 10 |
| Inca Red Crude Anthocyanin Extract (1%) | 4.8 ± 0.5 | 113 ± 10 |
| Inca Purple Crude Anthocyanin Extract (1%) | 5.2 ± 0.5 | 125 ± 10 |

Coefficient of repression of development of stomach cancer (%) = {1 − [Weight of tumors (g) of stomach cancer in mouse having ingested sample]/[Weight of tumors (g) of stomach cancer in mouse having ingested control group]} × 100

It is clear from Table 2 above that Inca red powder showed 44%, Inca purple powder 41%, Inca purple crude anthocyanin extract 50% and Inca red crude anthocyanin extract 44%, respectively of repression of the number of tumors of stomach cancer as compared with the control group and that Inca red powder showed 44%, Inca purple powder 42%, Inca purple crude anthocyanin extract 45% and Inca red crude anthocyanin extract 39%, respectively of repression of the weight of such tumors as compared with the control group.

As described above, since the apoptosis inductor of this invention which is formed of an anthocyanin-containing extract from an anthocyanin-containing potato uses as its raw material the anthocyanin-containing potato which the mankind are accustomed to take copiously as food, it can be consumed reassuredly and handily in the same manner as ordinary food and drink. Since it enjoys very high safety, inexpensiveness as compared with the conventional cancer depressants, and freedom from fear of side effects, it can be consumed continuously. Further, since this apoptosis inductor (anthocyanin-containing extract) excels in the tinting property, it exhibits a visual effect of affording colored foodstuffs particularly where it is consumed as incorporated in various foodstuffs.

What is claimed is:

1. A method for inducing gastric cancer cell apoptosis comprising a step of administering an anthocyanin-containing extract obtained from a potato containing anthocyanin in its skin and flesh to a subject in need thereof, wherein an acid or an acid alcohol is used as an extracting solvent; the extracting solvent contains not less than 1% of table salt; and a pH of the extracting solvent is not more than 3.0 and/or a temperature of the extracting solvent is not higher than 10° C.

2. The method of claim 1, wherein the potato is a cultivated species or a hybrid thereof.

3. The method of claim 2, wherein the cultivated potato is *Solanum tuberosum* ssp. *Andigena* or *S. phureja* Juz. Et Buk. or a hybrid thereof.

4. The method of claim 2, wherein the cultivated potato is *Solanum tuberosum* ssp. *Andigena* or *S. phureja* Juz. Et Buk.

5. The method of claim 1, wherein the acid is formic acid or trifluoroacetic acid.

6. The method of claim 1, wherein the acid is lactic acid, acetic acid or citric acid.

7. A method for inducing gastric cancer cell apoptosis, comprising:
extracting a potato containing anthocyanin in its skin and flesh with an extracting solvent comprises an acid or an acid alcohol, wherein the pH of the extracting solvent is not more than 3.0 and/or the temperature of the extracting solvent is not higher than 10° C. to produce an extract containing anthocyanin, and
administering the extract to a subject in need thereof.

8. The method of claim 7, wherein the potato is a cultivated species or a hybrid thereof.

9. The method of claim 8, wherein the cultivated potato is *Solanum tuberosum* ssp. *Andigena* or *S. phureja* Juz. Et Buk. or a hybrid thereof.

10. The method of claim 8, wherein the cultivated potato is *Solanum tuberosum* ssp. *Andigena* or *S. phureja* Juz. Et Buk.

11. The method of claim 7, wherein the acid is formic acid or trifluoroacetic acid.

12. The method of claim 7, wherein the acid is lactic acid, acetic acid or citric acid.

13. In a process for inducing gastric cancer cell apoptosis in a subject in need thereof, the improvement comprising obtaining an extract containing anthocyanin by extracting a potato containing anthocyanin in its skin and flesh with an extracting solvent comprising an acid or an acid alcohol, wherein the pH of the extracting solvent is not more than 3.0 and/or the temperature of the extracting solvent is not higher than 10° C. and administering the extract to the subject.

14. The method of claim 13, wherein the potato is a cultivated species or a hybrid thereof.

15. The method of claim 14, wherein the cultivated potato is *Solanum tuberosum* ssp. *Andigena* or *S. phureja* Juz. Et Buk. or a hybrid thereof.

16. The method of claim 14, wherein the cultivated potato is *Solanum tuberosum* ssp. *Andigena* or *S. phureja* Juz. Et Buk.

17. The method of claim 13, wherein the acid is formic acid or trifluoroacetic acid.

18. The method of claim 13, wherein the acid is lactic acid, acetic acid or citric acid.

19. A method for inducing gastric cancer cell apoptosis comprising administering an anthocyanin-containing extract obtained from a potato containing anthocyanin in its skin and flesh to a subject in need thereof, wherein an acid or an acid alcohol is used as an extracting solvent; the acid is lactic acid or acetic acid; and a pH of the extracting solvent is not more than 3.0, and/or a temperature of the extracting solvent is not higher than 10° C.

* * * * *